United States Patent
Iijima et al.

(10) Patent No.: US 9,638,640 B2
(45) Date of Patent: May 2, 2017

(54) AUTOMATIC ANALYZER

(71) Applicant: HITACHI HIGH-TECHNOLOGIES CORPORATION, Tokyo (JP)

(72) Inventors: Masahiko Iijima, Tokyo (JP); Akihisa Makino, Tokyo (JP); Manabu Ando, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 52 days.

(21) Appl. No.: 14/413,447

(22) PCT Filed: Jul. 8, 2013

(86) PCT No.: PCT/JP2013/068584
§ 371 (c)(1),
(2) Date: Jan. 8, 2015

(87) PCT Pub. No.: WO2014/017277
PCT Pub. Date: Jan. 30, 2014

(65) Prior Publication Data
US 2015/0204794 A1   Jul. 23, 2015

(30) Foreign Application Priority Data

Jul. 24, 2012 (JP) ................................. 2012-163213

(51) Int. Cl.
*G01N 21/75* (2006.01)
*G01N 1/38* (2006.01)
(Continued)

(52) U.S. Cl.
CPC ............... *G01N 21/75* (2013.01); *G01N 1/38* (2013.01); *G01N 21/47* (2013.01); *G01N 21/59* (2013.01);
(Continued)

(58) Field of Classification Search
CPC .................................. G01N 1/38; G01N 21/75
See application file for complete search history.

(56) References Cited

U.S. PATENT DOCUMENTS 4,451,433 A    5/1984 Yamashita et al.

FOREIGN PATENT DOCUMENTS

JP      2001-141654        5/2001
WO   WO 2013160425 A1 * 10/2013 ........... G01N 21/274

OTHER PUBLICATIONS

Yamamoto et al., Journal of Japan Society of Clinical Chemistry, Clinical Chemistry, vol. 40, (2011), p. 149-157, "Guidlines for Validation Regarding Quantitative Analysis," written by Japan Society of Clinical Chemistry, Expert Committee of Quality Management, Project on Guildelines for Validation Regarding Quantitative Analysis.

(Continued)

*Primary Examiner* — P. Kathryn Wright
(74) *Attorney, Agent, or Firm* — Mattingly & Malur, PC (57) ABSTRACT

An automatic analyzer which can reduce the effort necessary for conducting a test of limit of detection/limit of quantification properties and managing the test results is provided. Operation condition-setting means for conducting an evaluation test for at least one of a limit of detection and a limit of quantification for each measurement item, determination condition-setting means for setting a determination condition of the evaluation test, and a calculation unit for obtaining a measurement result of a dilution series containing different dilution concentrations by controlling the sample-dispensing mechanism, the reagent-dispensing mechanism and the measurement unit based on the set operation condition, and calculating a test result of the evaluation test from the measurement result of the dilution series based on the set determination condition are disposed.

7 Claims, 8 Drawing Sheets

(51) Int. Cl.
*G01N 21/47* (2006.01)
*G01N 35/00* (2006.01)
*G01N 21/59* (2006.01)
*G01N 35/04* (2006.01)

(52) U.S. Cl.
CPC .................. *G01N 35/00603* (2013.01); *G01N 2035/0446* (2013.01); *G01N 2201/02* (2013.01); *G01N 2201/061* (2013.01); *G01N 2201/12* (2013.01)

(56) References Cited

OTHER PUBLICATIONS

JAIMAS, Standards of Japan Analytical Instruments Manufactures' Association, Method for Displaying Properties of Clinical Automatic Analyzer (JAIMAS 0011-2011), established on Jan. 19, 2011, p. 56-59, published by Japan Analytical Instruments Manufactures' Association.

* cited by examiner

```
╭─────────────────────────────────────────────────────────────────────╮
│        SCREEN FOR SETTING DETERMINATION CONDITION OF DETECTION/QUANTIFICATION LIMIT TEST        │
│                                                                     │
│   ITEM NAME   | CRP        ▼ |                                      │
│                                                                     │
│  ┌──────────────────────────────┐  ┌──────────────────────────────┐ │
│  │ METHOD FOR DETERMINING LIMIT │  │ METHOD FOR DETERMINING LIMIT │ │
│  │ OF DETECTION                 │  │ OF QUANTIFICATION            │ │
│  │                              │  │                              │ │
│  │  ● METHOD THAT CLSI (NCCLS)  │  │  REGRESSION  | EXPONENTIAL   ▼│ │
│  │    RECOMMENDS                │  │  EQUATION    | FUNCTION       │ │
│  │                              │  │              | APPROXIMATION  │ │
│  │  ○ 3SD METHOD                │  │                              │ │
│  │                              │  │  ● ALLOWABLE LIMIT CV 20%    │ │
│  │  ○ 2SD METHOD                │  │                              │ │
│  │                              │  │  ○ ALLOWABLE LIMIT CV 10%    │ │
│  │  ○ | 2.6 | SD METHOD         │  │                              │ │
│  │                              │  │  ○ ALLOWABLE LIMIT CV | 5 | %│ │
│  └──────────────────────────────┘  └──────────────────────────────┘ │
╰─────────────────────────────────────────────────────────────────────╯
```

FIG. 6

| ITEM NAME | UNIT | LIMIT OF BLANK | LIMIT OF DETECTION | LIMIT OF QUANTIFICATION | DATE OF OPERATION |
|---|---|---|---|---|---|
| AAA | mg/dL | 0.002 | 0.004 | 0.008 | YYYY/MM/DD |
| BBB | ng/mL | 0.1 | 0.2 | 0.3 | YYYY/MM/DD |
| CCC | U/mL | 0.3 | 0.5 | 1.2 | YYYY/MM/DD |
|  |  |  |  |  |  |
|  |  |  |  |  |  |

FIG. 7

| RANGE OF MEASUREMENT RESULTS | PROVIDED INFORMATION | REEXAMINATION CONDITION |
|---|---|---|
| LESS THAN LIMIT OF BLANK | NOT DETECTED | NOT REEXAMINED ▼ |
| LIMIT OF BLANK OR MORE TO LESS THAN LIMIT OF DETECTION | SUSPENSION OF DETERMINATION | INCREASE IN AMOUNT ▼ |
| LIMIT OF DETECTION OR MORE TO LESS THAN LIMIT OF QUANTIFICATION | DETECTED BUT QUANTIFICATION FAILED | INCREASE IN AMOUNT ▼ |
| LIMIT OF QUANTIFICATION OR MORE | (NOT PROVIDED) | NOT REEXAMINED ▼ |

SCREEN FOR SETTING PROVIDED INFORMATION OF MEASUREMENT RESULTS/REEXAMINATION

ITEM NAME: AAA

FIG. 8

ITEM NAME: AAA  UNIT: mg/dL

| INDEX | DATE OF TEST | TEST RESULTS | ALLOWABLE RANGE CHECK VALUE |
|---|---|---|---|
| LIMIT OF BLANK | YYYY/MM/DD | 0.002 | 0.004 |
| LIMIT OF DETECTION | YYYY/MM/DD | 0.004 | 0.006 |
| LIMIT OF QUANTIFICATION | YYYY/MM/DD | 0.008 | 0.010 |

AUTOMATIC ANALYZER

TECHNICAL FIELD

The present invention relates to an automatic analyzer which analyzes components of biological samples such as blood and urine, and especially relates to an automatic analyzer which is used for analyzing examination items for which a limit of detection and a limit of quantification are clinically important.

BACKGROUND ART

An automatic analyzer which applies a light from a light source to a reaction solution obtained by mixing a biological sample, such as blood serum and urine, and a reagent, calculates the absorbance from the change of the amount of the transmitted light at a certain wavelength and determines the concentration of a substance measured according to the Lambert-Beer law is widely used (for example, PTL 1).

There are two types of reaction which are measured by an automatic analyzer, namely a color reaction mainly due to the reaction of a substrate and an enzyme and immune agglutination of an antigen and an antibody. An analysis using the former reaction is called a biochemical analysis and its examination items are enzymes, lipids, nitrogen compounds and the like. An analysis using the latter reaction is called an immunoassay and its examination items include microproteins, tumor markers, hormones, drugs in the blood and the like. Among the substances that are measured in the latter analysis, there are examination items in which detection with high sensitivity in a low-concentration range is required and examination items in which the quantitative value is important for the clinical diagnosis. For these items, latex immuno-nephelometry using latex particles with surfaces sensitized (bound) with an antibody as a sensitizer is used. In latex immuno-nephelometry, a light is applied to aggregates generated by the aggregation of the latex particles due to the substance to be measured, and the change of the amount of the light which has been transmitted without being scattered is measured. Because the change of the light amount after a certain period of time becomes larger as the concentration of the substance to be measured becomes higher, the concentration of the substance to be measured can be calculated from the change of the amount of the transmitted light.

Recently, it has been desired that the sensitivity of immunoassay be further improved. So far, it has been attempted to measure the scattered light, rather than the transmitted light, in an apparatus for performing latex immunoassay with higher sensitivity. Such alight scattering spectrophotometer is called a nephelometer and measures the intensity of the scattered light by applying a light to aggregates generated by the reaction of an antigen contained in a sample and an antibody contained in a reagent. For example, PTL 2 discloses an apparatus which separates the transmitted light and the scattered light using a diaphragm and measures the absorbance and the scattered light simultaneously.

In order to ensure the reliability and the adequacy of measurement results obtained using these automatic analyzers, various characteristics have been defined as objects for confirming the adequacy of a measurement method. For example, NPL 1 describes that limit of detection/limit of quantification is inspected in addition to the accuracy and the precision, as a characteristic which needs to be confirmed for the adequacy. A limit of detection is the lowest amount of a substance to be measured in a sample that can be detected, and a limit of quantification is the lowest amount of a substance to be measured at which the amount can be measured with a certain level of precision. A method for evaluating limit of detection/limit of quantification is described in NPL 2 for example.

In the present specification, a term "limit of detection/limit of quantification" is used for the sake of convenience. When described in this way, the term is used to mean at least one of a limit of detection and a limit of quantification and includes all the cases of a limit of detection only, a limit of quantification only, and a limit of detection and a limit of quantification.

CITATION LIST

Patent Literature

PTL 1: U.S. Pat. No. 4,451,433
PTL 2: JP-A-2001-141654

Non Patent Literature

NPL 1: Journal of Japan Society of Clinical Chemistry, Clinical Chemistry, Vol. 40 (2011), p. 149-157, "Guidelines for Validation Regarding Quantitative Analysis", Written by Japan Society of Clinical Chemistry, Expert Committee of Quality Management, Project on Guidelines for Validation Regarding Quantitative Analysis NPL 2: Standards of Japan Analytical Instruments Manufacturers' Association, Method for Displaying Properties of Clinical Automatic Analyzer (JAIMAS 0011-2011), established on Jan. 19, 2011, p. 56-59, published by Japan Analytical Instruments Manufacturers' Association

SUMMARY OF INVENTION

Technical Problem

When the limit of detection/limit of quantification of an analysis method was evaluated using automatic analyzers such as those of PTL 1 and PTL 2, the evaluation test would be mostly conducted manually by a tester.

A method for evaluating the limit of detection/limit of quantification mainly consists of four steps. The first step is a step for preparing dilution series samples containing a substance to be measured at concentrations around the limit of detection/limit of quantification. The second step is a step for measuring the prepared dilution series samples with an automatic analyzer. The third step is a step for plotting the dispersions of the actual values relative to the theoretical concentrations, using the average values and the standard deviations of the measurement results, variation coefficients and the like. The fourth step is a step for comparing the plotted results and the determination criteria and determining the evaluation results of the limit of detection/limit of quantification. The steps except for the second step require complicated operations by the tester.

For this reason, although a limit of detection/limit of quantification test has been conducted when an apparatus has been installed or a reagent has been introduced, the test has seldom been carried out at regular intervals. Thus, the test results would hardly reflect the adequacy confirmation of the measurement using the apparatus or the reagent in the most recent state.

Moreover, also with respect to test results of the limit of detection/limit of quantification, an operator has manually calculated the properties and managed the results, and thus results considering the most recent limit of detection/limit of quantification properties have not been reported, regarding results of an individual specimen measured with an automatic analyzer.

An object of the invention is to provide an automatic analyzer which reduces the operations of a tester by automating a limit of detection/limit of quantification test and contributes to ensuring the reliability and the adequacy of the measurement results by applying the test results to the output of results of normal patient specimens and the like.

Solution to Problem

The constitution of the invention to achieve the above object is as follows.

The constitution is an automatic analyzer having a sample-dispensing mechanism for dispensing a sample to a reaction container, a reagent-dispensing mechanism for dispensing a reagent to the reaction container, a measurement unit for optically measuring a mixture of the sample and the reagent, operation condition-setting means for conducting an evaluation test for at least one of a limit of detection and a limit of quantification for each measurement item, determination condition-setting means for setting a determination condition of the evaluation test, and a calculation unit for obtaining a measurement result of a dilution series containing different dilution concentrations by controlling the sample-dispensing mechanism, the reagent-dispensing mechanism and the measurement unit based on the set operation condition, and calculating a test result of the evaluation test from the measurement result of the dilution series based on the set determination condition.

Advantageous Effects of Invention

According to the automatic analyzer described in the invention, the operations of an operator for the evaluation of the limit of detection/limit of quantification can be reduced.

In addition, by using the limit of detection/limit of quantification properties which reflect the most recent state of an apparatus or a reagent for outputting measurement results of a normal specimen or for determining whether a reexamination is necessary or not, it becomes possible to provide data with high reliability in the measurement of a normal specimen.

DESCRIPTION OF EMBODIMENTS

Embodiments of the invention are explained below using drawings.

Figure 1:
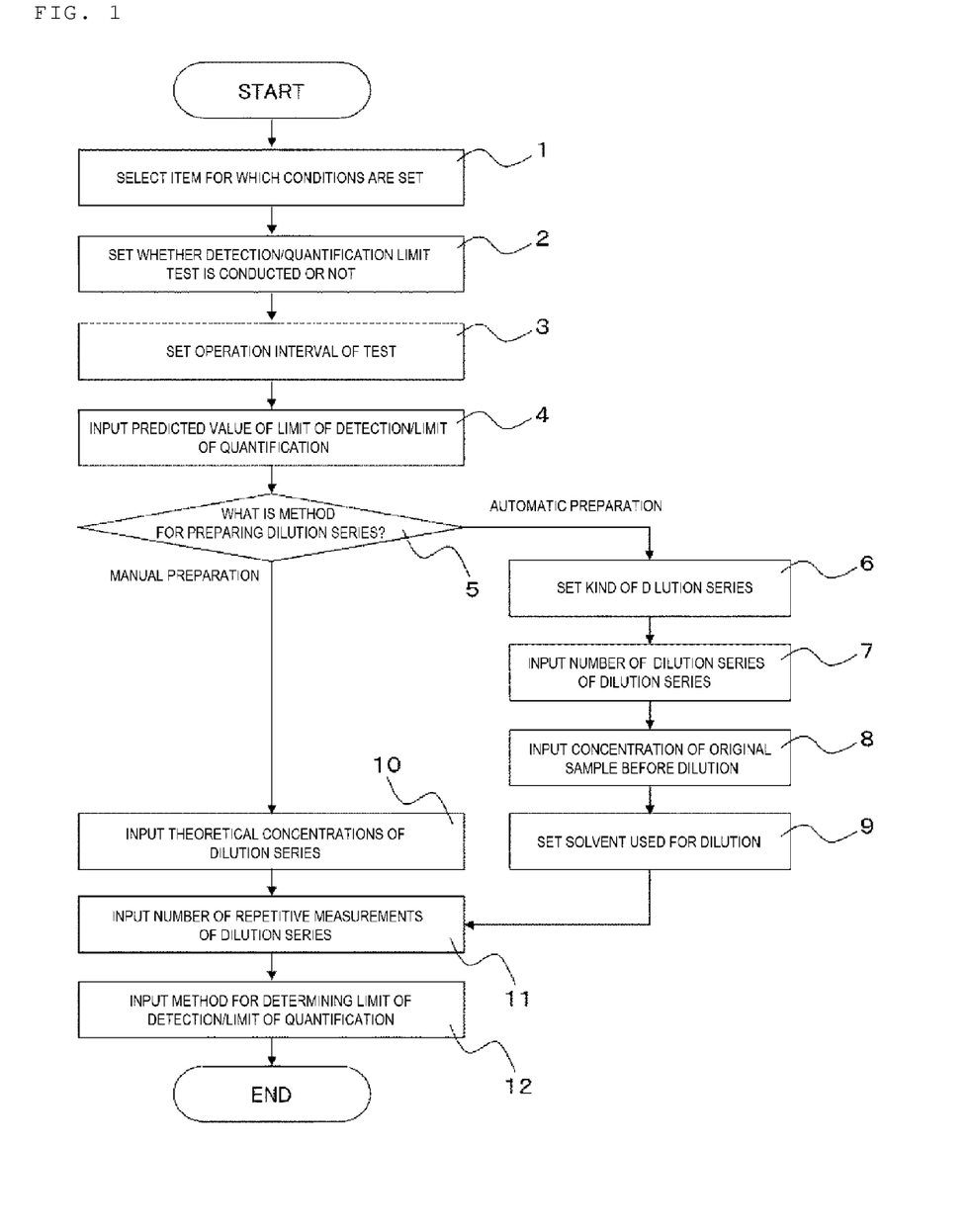
FIG. 1 A flow chart showing treatments necessary for setting evaluation test conditions of the limit of detection/limit of quantification, in an automatic analyzer to which the invention is applied.

FIG. 1 is a flow chart showing treatments necessary for setting evaluation test conditions of the limit of detection/limit of quantification, in an automatic analyzer to which the invention is applied.

In a step 1, an operator first selects an item for which the limit of detection/limit of quantification test should be conducted. Because it is not always necessary to test the limit of detection/limit of quantification for all the items to be analyzed by the apparatus, an item for which the properties are particularly required should be selected.

Next, it is set in a step 2 whether each of the limit of detection and limit of quantification tests should be conducted or not for the item selected in the step 1. In a step 3, the interval for conducting the limit of detection/limit of quantification test is set. In a step 4, the predicted value of the limit of detection/limit of quantification is input.

In a step 5, a method for preparing a dilution series used for the test is selected. In order to reduce the operations of the operator for preparing the dilution series, it is needless to say that the automatic preparation by the apparatus to which the invention is applied is desirable. However, since there are many complicated operations among the operations for just calculating the limit of detection/limit of quantification from measurement results of a dilution series, a flow in which the test is conducted using a manually prepared dilution series is also acceptable.

When the dilution series is prepared using the automatic preparation by the apparatus, the kind of dilution series and the number of dilution series are set in subsequent steps 6 and 7. In a step 8, the concentration of the original sample for preparing the dilution series is input. In a step 9, the kind of the solvent used for preparing the dilution series is set.

On the other hand, when the test is conducted using a manually prepared dilution series, the theoretical concentrations of the dilution series are input in a step 10. In case of an automatically prepared dilution series, the concentration of the original sample before the dilution and the dilution condition have already been input in the apparatus and thus it is not necessary to input the theoretical concentrations.

Next, the number of repetitive measurements of the dilution series samples is input in a step 11. Lastly, a method for determining the limit of detection/limit of quantification is input in a step 12.

The steps for setting the evaluation test conditions shown in FIG. 1 are merely those of an Example. As long as test results of the limit of detection/limit of quantification can be obtained at the end, some of the steps may be skipped. For example, in an embodiment in which the limit of detection/ limit of quantification test is manually conducted in case of necessity, the steps 2 to 4 may be omitted.

Figure 2:
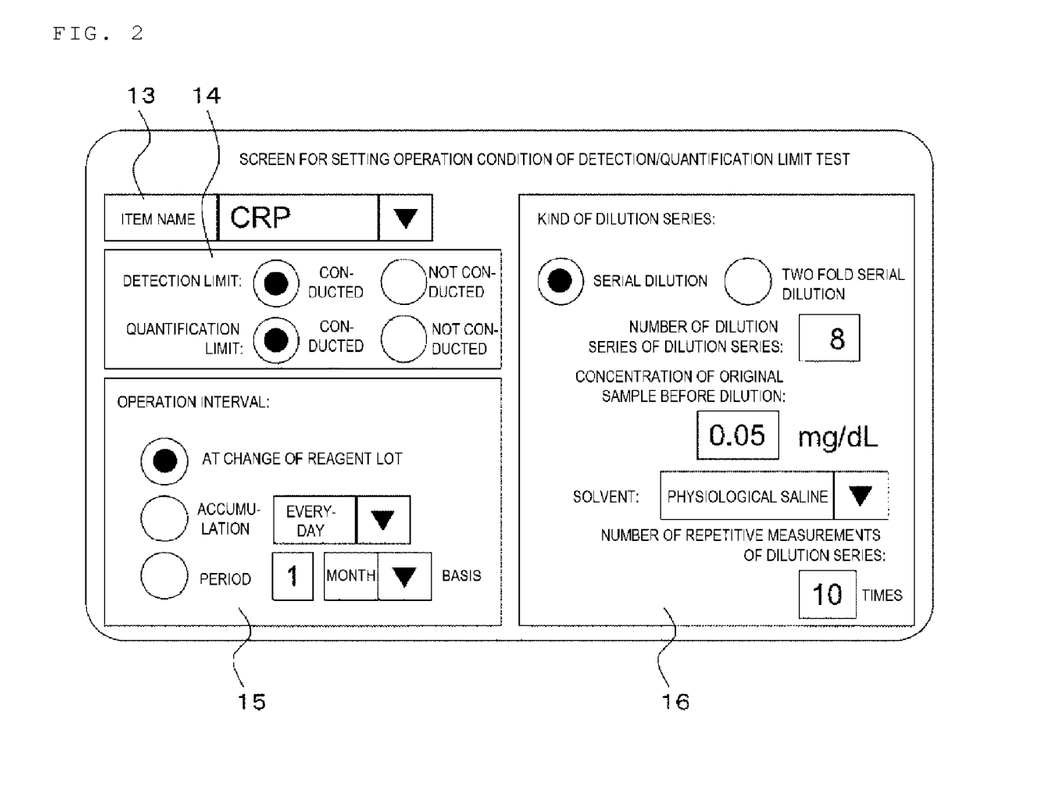
FIG. 2 A diagram showing an example of a screen for setting an operation condition of a limit of detection/limit of quantification test for each item, in an automatic analyzer to which the invention is applied.

FIG. 2 is a diagram showing an example of a screen for setting an operation condition of the limit of detection/limit of quantification test for each item, in an automatic analyzer to which the invention is applied.

A box 13 for selecting the item is used for the setting in the step 1. FIG. 2 shows an example of a screen for setting the operation condition of the test after selecting the item name from a pull-down list. However, the screen constitution may be a table or the like in which test operation conditions of more than one item can be set as a list.

A box 14 for setting whether the limit of detection/limit of quantification test should be conducted or not is used for the setting in the step 2. Although it is not shown in FIG. 2, it is possible to provide an option of testing the limit of blank only, separately from the limit of detection/limit of quantification test. In this regard, the descriptions of Examples of the limit of detection/limit of quantification test in the invention similarly apply to the evaluation test of the limit of blank.

A box 15 for setting the operation interval of the limit of detection/limit of quantification test is used for the setting in the step 3. Regarding examples of the interval of the test operations, an option of testing each time a reagent lot is changed, an option of testing at periodic intervals (for example, once a month), an option of calculating the test results using the accumulated measurement results, and the like can be thought as Examples. An example of the method in which the accumulated measurement results are used is a method in which the dilution series is measured twice a day and the daily limit of detection/limit of quantification is calculated from the measurement results of the most recent five days.

In a box 16 for setting the method for preparing the dilution series/the number of measurements, a setting example of conditions necessary for the automatic preparation of the dilution series by the apparatus is shown. As the kinds of dilution series which can be selected, it is more preferable that a selection can be made from serial dilution such as a series of concentrations of zero tenth, one tenth, two tenths, . . . and ten tenths (the total number of dilution series=11), two fold serial dilution such as a series of concentrations of one 64th, one 32nd, . . . a half and one (the total number of dilution series=8), and the like.

As shown in FIG. 2, by setting the number of the dilution series, the concentration of the original sample before the dilution used for the preparation and the kind of solvent, the apparatus can automatically prepare the dilution series. In this case, it is desirable to prepare the dilution series in such a way that the highest concentration of the dilution series is a little higher than the predicted value of the limit of detection/limit of quantification, which has been input in the step 4 of FIG. 1, for example a concentration which is 1.5 times as high as the predicted value of the limit of detection/limit of quantification. The apparatus can prepare in such a way by setting a certain fold dilution, such as a concentration 1.5 times as high as the predicted value, as the highest concentration of the dilution series. Measurement of a high concentration that is totally different from the predicted value, for example ten times as high as the predicted value, is useless in the limit of detection/limit of quantification test, and waste of the reagent and the like can be avoided by avoiding such a useless test. On the other hand, in case the number of the dilution series is the same, by preparing the dilution series based on the predicted value, it is possible to test using measurement results of more dilution series around the limit of detection/limit of quantification, and thus results with higher precision can be obtained.

In addition, an input box for setting the number of repetitive measurements of each dilution series is also provided. For all the samples of the dilution series, the measurement is conducted for the set number of repetitive measurements.

Figure 3:
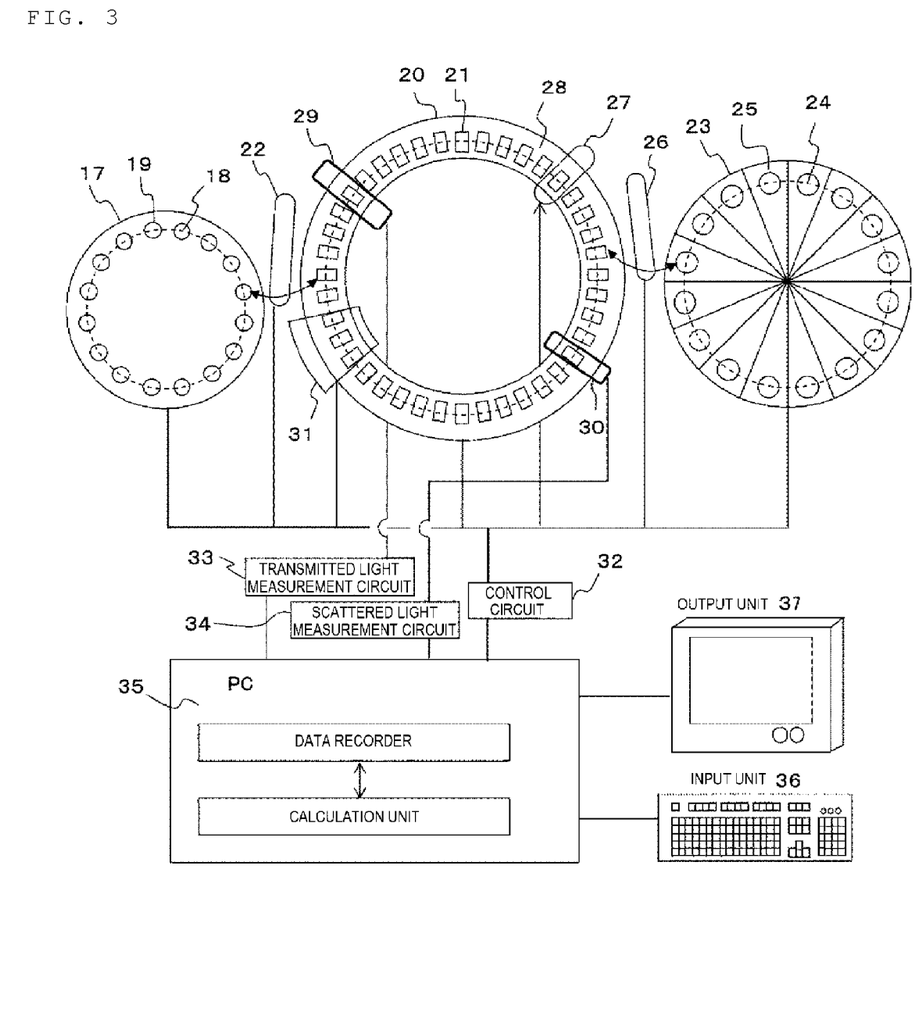
FIG. 3 A block diagram showing an example of an apparatus constitution of an automatic analyzer to which the invention is applied.

FIG. 3 is a block diagram showing an example of an apparatus constitution of an automatic analyzer to which the invention is applied. A sample disk 17, sample containers 19 which are disposed on a circle concentric with the sample disk 17 and hold samples 18, a reaction disk 20, reaction containers 21 disposed on a circle concentric with the reaction disk 20, a sample-dispensing mechanism 22, a reagent disk 23, reagent containers 25 which are disposed on a circle concentric with the reagent disk 23 and contain various reagents 24, a reagent-dispensing mechanism 26, a stirring mechanism 27, a thermostat bath-circulating liquid 28, a transmitted light measurement unit 29, a scattered light measurement unit 30, and a reaction container-washing mechanism are disposed on the apparatus. A control circuit 32, a transmitted light measurement circuit 33, a scattered light measurement circuit 34, a PC 35, an input unit 36, and an output unit 37 are disposed in the analyzer.

The normal analysis by the automatic analyzer is conducted according to the following orders. First, the sample 18 set on the sample disk 17 is dispensed from the sample container 19 to the reaction container 21 by the sample-dispensing mechanism 22. The reaction container containing the sample moves to a reagent-dispensing position due to the rotation of the reaction disk 20 and the reagent-dispensing mechanism 26 dispenses the reagent 24 to be used for the analysis from the reagent container 25 to the reaction container 21. Then, the stirring mechanism 27 stirs the mixture in the reaction container. The temperature of the reaction container 21 is kept constant, for example at 37° C., by the thermostat bath-circulating liquid 28 filled under the reaction disk 20, resulting in the progress of the reaction and the stabilization of the progress of the reaction. When the mixture in the reaction container 21 passes through the transmitted light measurement unit 29 due to the rotation of the reaction disk 20, the amount of the transmitted light is measured through the transmitted light measurement circuit 33; and the amount of the scattered light is measured through the scattered light measurement circuit 34 when the mixture passes through the scattered light measurement unit 30. The data of the transmitted light amount and the data of the scattered light amount thus obtained are sent to the PC 35, and the concentration of the subject component in the sample is calculated by the calculation unit in the PC while the data are recorded in the data recorder and the calculated results are displayed on the output unit 37. The reaction container 21 after the reaction is washed by the reaction container-washing mechanism 31 and used again for the next reaction.

When a manually prepared dilution series is used in the step 5 in FIG. 1, the dilution series is set on the sample disk 17 and the dilution series is measured in the same manner as in the flow of the normal analysis described above.

When the dilution series is automatically prepared by the apparatus, the original sample before the dilution set on the sample disk 17 and a solvent for diluting the sample, such as physiological saline, which is set on the reagent disk 23 are dispensed in the same reaction container 21 and stirred by the stirring mechanism 27, thereby diluting the sample. The dilution series is prepared by preparing dilution series with different mixing ratios of the original sample before the dilution and the solvent (for example, original sample before dilution:solvent=0:10, 1:9, 2:8, . . . 9:1, 10:0 and the like) in the reaction containers. Another acceptable Example of the automatic preparation is a constitution in which diluted samples of two fold serial dilution are prepared by first preparing a diluted sample in a large amount in a first reaction container, dispensing a certain amount of the diluted sample in a second reaction container and adding the same amount of the solvent to obtain a diluted sample of a half concentration, and repeating the similar dilution in third and fourth reaction containers.

The dilution series prepared in the reaction containers are dispensed again to other reaction containers by the sample-dispensing mechanism and then measured according to the flow of the normal analysis.

The solvent used for diluting the sample is not necessarily in the reagent disk, but the solvent may be at a set position outside the reagent disk. In the sample-dispensing mechanism 22 and the reagent-dispensing mechanism 26, the flow paths of the mechanisms are filled with purified water for purposes of transmitting a pressure for the dispensing operation and washing insides of dispensing nozzles, and thus a constitution in which purified water is used as the solvent for diluting the sample is also acceptable.

Similarly, the original sample before the dilution is not necessarily set in the sample disk immediately before the test, but the original sample may be previously set in the apparatus in a state in which the sample is prevented from being concentrated or degenerated. A possible example is a constitution in which the original sample for preparing the dilution series is kept at an exclusive position on the sample disk 17 or on another exclusive sample disk which is cooled, which is for setting a standard solution used for the calibration of the apparatus or a sample for controlling the precision, and the dilution series is automatically prepared at a set time.

In this regard, although explanations have been made referring to an automatic analyzer having both of the transmitted light measurement unit 29 and the scattered light measurement unit 30, at least one of the measurement units for conducting optical measurement is sufficient and it is not necessary that both are disposed. However, because in general, measurement of a low concentration with high sensitivity is possible with the scattered light measurement, it is desirable that the scattered light measurement unit 30 is provided in the limit of detection/limit of quantification test.

Figure 4:
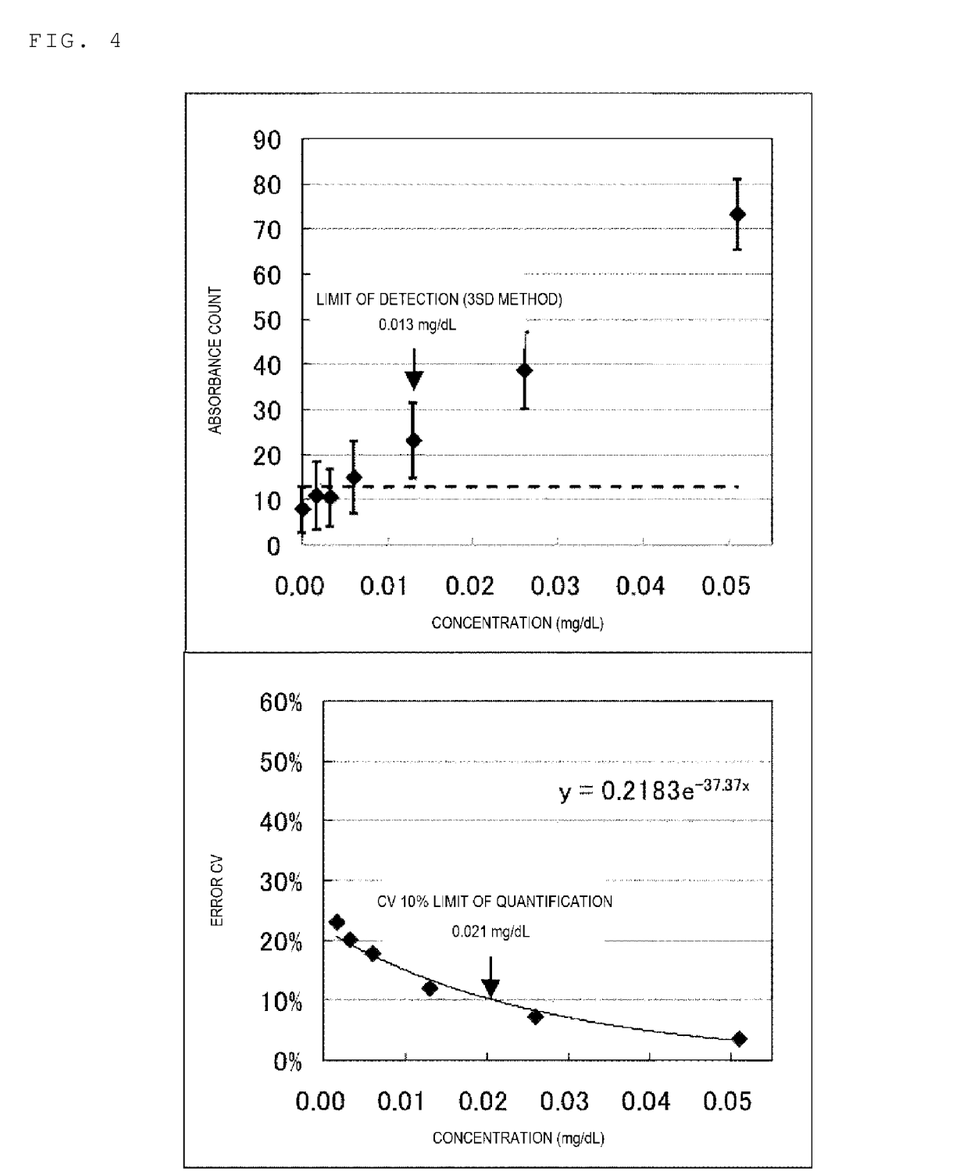
FIG. 4 A diagram showing an example of processes for calculating the limit of detection/limit of quantification from measurement results of a dilution series, in an automatic analyzer to which the invention is applied.

FIG. 4 is a diagram showing an example of processes for calculating the limit of detection/limit of quantification from the measurement results of the dilution series, in an automatic analyzer to which the invention is applied. The upper chart in FIG. 4 is an example for calculating the limit of detection by 3SD method and the lower chart in FIG. 4 is an example for calculating the CV 10% limit of quantification. A series of calculation is performed by the calculation unit of the PC 35.

In the upper chart in FIG. 4, the theoretical concentration of each dilution series is plotted on the horizontal axis, and the average value and the dispersion of the absorbance counts (3SD values) of the repetitive measurements of each sample are indicated on the vertical axis with an error bar. The upper limit of dispersion at a concentration of 0.00 mg/dL (a blank sample) is indicated with a dotted line in the chart. In 3SD method, the upper limit of dispersion of the blank measurement and the lower limit of dispersion of the measurement of each dilution series are compared, and the concentration at which the upper limit of dispersion of the blank measurement is smaller than the lower limit of dispersion of the measurement of the dilution series is determined to be the limit of detection (0.013 mg/dL in the example shown in FIG. 4). Methods for determining the limit of detection include a method using 2SD, a method in which a 5% critical rate and a combined standard deviation in standard normal distribution are used and which National Committee for Clinical Laboratory Standards of the U.S. (NCCLS, which is now CLSI) recommends, and the like, in addition to the above method.

In the lower chart in FIG. 4, the theoretical concentration of each dilution series is plotted on the horizontal axis, and the error CV of the absorbance counts in the repetitive measurements of each sample is shown on the vertical axis. The curve in the chart corresponds to an equation of an approximate curve created by curve fitting of the errors CV using an exponential function. The concentration at which the approximate curve and the allowable limit of error (CV 10% in this case) cross each other, namely 0.021 mg/dL, is determined to be the CV 10% limit of quantification. For the curve fitting method of the errors CV, a cumulative approximation, a polynomial approximation using a quadratic function or a cubic function and the like may be used, in addition an exponential function.

Figure 5:
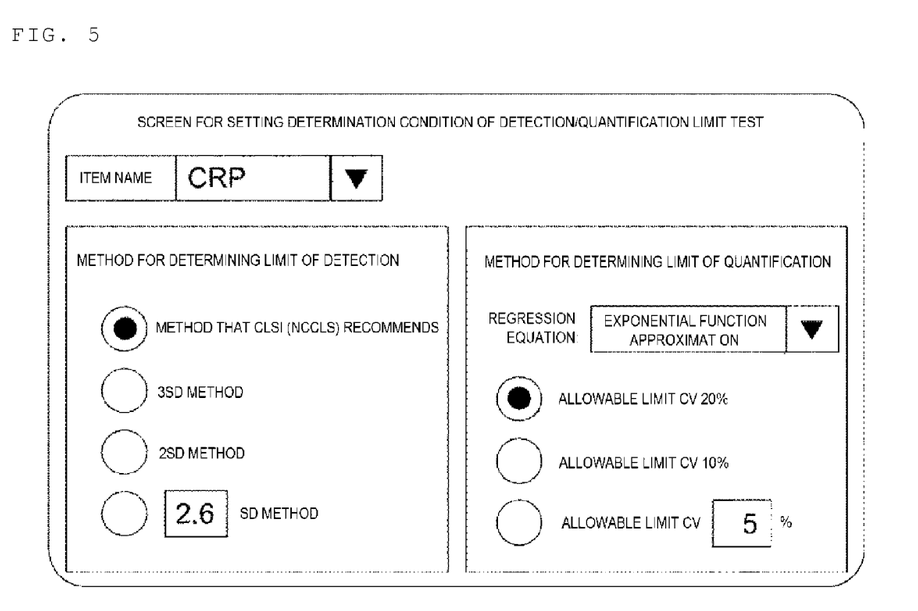
FIG. 5 A diagram showing an example of a screen for setting a determination condition of results of a limit of detection/limit of quantification test, in an automatic analyzer to which the invention is applied.

FIG. 5 is a diagram showing an example of a screen for setting a determination condition of the results of the limit of detection/limit of quantification test, in an automatic analyzer to which the invention is applied. An example for setting the method for determining the limit of detection is shown in the left half of the screen and an example for setting the method for determining the limit of quantification is shown in the right half of the screen. For both of the methods for determining the limit of detection and the limit of quantification, the constitution may be a constitution in which one determination method is selected from more than one method, or a constitution in which more than one determination method can be selected at the same time and the test results of the determination methods are displayed together in a screen displaying the test results of the limit of detection. In addition, another acceptable constitution is that the SD range and the allowable limit CV value used for the determination are input as shown at the last lines of the boxes for setting the determination methods. Another acceptable constitution is that an equation for curve fitting used for calculating the limit of quantification is selected from an exponential function approximation, a cumulative function approximation and a polynomial approximation, or a regression method with which the difference from the fitted curve is small is automatically selected.

Figure 6:
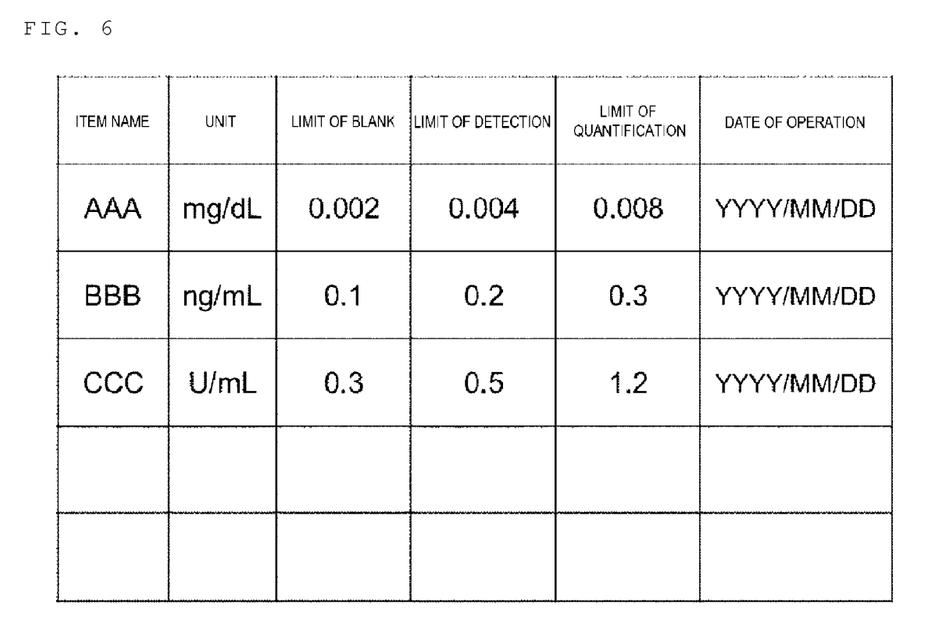
FIG. 6 A diagram showing an example for outputting results of a limit of detection/limit of quantification test, in an automatic analyzer to which the invention is applied.

FIG. 6 is a diagram showing an example for outputting the results of the limit of detection/limit of quantification test, in an automatic analyzer to which the invention is applied. FIG. 6 shows an example for displaying a table of the test results of the limit of blank, the limit of detection and the limit of quantification for all the items for which the limit of detection/limit of quantification test has been conducted. A desirable constitution is that the details of the measurement results of a dilution series as shown in FIG. 4 can be checked by selecting the item on the screen of FIG. 6. This is because, by displaying not only the test results of the limit of detection/limit of quantification but also these charts on the output unit 37, the operator can measure a dilution series again with its middle near the limit of detection or determine whether the operation condition or the determination condition needs to be changed.

Furthermore, in another Example of the method for displaying the test results, it is desirable to record the results of the previous limit of detection/limit of quantification tests in the data recorder of the analyzer PC 35, and another possible screen constitution is that the test dates are plotted on the horizontal axis and the test results are plotted on the vertical axis so that the change of the limit of detection/limit of quantification properties with time can be checked, although such a constitution is not shown in the drawings. From this, for example, the operator can more easily recognize a rapid change of the limit of detection/limit of quantification properties at a time of the change of a reagent lot or gradual deterioration of the limit of detection/limit of quantification properties by neglecting the maintenance of the apparatus.

Figure 7:
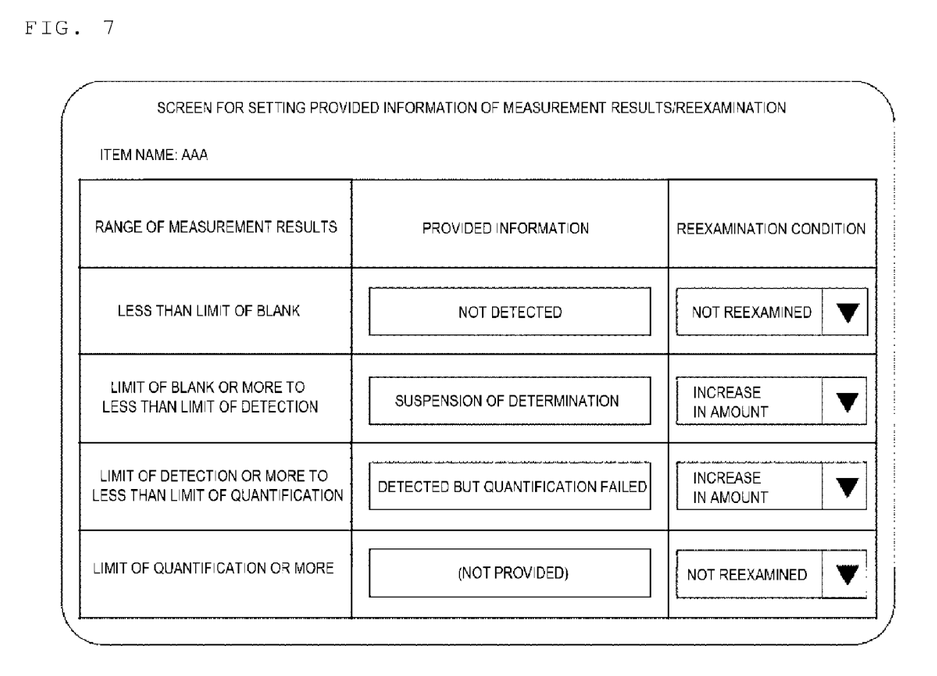
FIG. 7 A diagram showing an example of a screen for various settings for measurement results of a normal examination sample, in an automatic analyzer to which the invention is applied.

FIG. 7 is a diagram showing an example of a screen for various settings for the measurement results of a normal examination sample, in an automatic analyzer to which the invention is applied. The left column in the screen shows the range categories of the measurement result value of a patient specimen in a normal examination, the column in the middle shows the information provided with the measurement results of each range, and the right column shows an example of the reexamination condition of each range.

When the measurement results of a patient specimen or the like are calculated in the normal examination, the test results of the limit of blank, the limit of detection and the limit of quantification that the apparatus has recorded are compared with the measurement results of the normal examination, and depending on the concentration range in which the measurement results fall, the provided information which has been previously set is output with the measurement results.

For example, in the apparatus of the setting example of FIG. 7, when the measurement results of a patient specimen fall in the concentration range from the limit of blank or more to less than the limit of detection, the provided information "suspension of determination" is output with the measurement result value, thereby alerting the operator and reexamining the same specimen but in an increased amount. In addition, when the measurement results fall in the concentration range from the limit of detection or more to less than the limit of quantification, the provided information "detected but quantification failed" is output with the measurement result value, thereby alerting the operator and reexamining the same specimen but in an increased amount.

With respect to the provided information, it is desirable that the operator can choose whether the information should be provided or not and edit the provided information. With respect to the reexamination condition, the apparatus may reexamine automatically, or the apparatus may merely recommend the reexamination condition and follow the decision of the operator as to whether the reexamination should be conducted or not.

Thus, by setting the provided information given when reporting the examination results of the normal examination for each range based on the test results and allowing the calculation unit to output the provided information of the range containing the measurement results with the normal measurement results, it is possible to attract the attention on the reliability of the measurement results regarding the limit of detection/limit of quantification. In addition, when the apparatus reexamines automatically, the operations of the operator can be reduced by setting the reexamination condition of the normal examination for each range based on the test results and reexamining the same sample based on the set reexamination condition.

Although four kinds of measurement result range, namely a range less than the limit of blank, a range from the limit of blank to less than the limit of detection, a range from the limit of detection to less than the limit of quantification, and a range of the limit of quantification or more, have been described above, this is an example and it is sufficient that with respect to the ranges serving as the basis, at least the value of the limit of detection/limit of quantification test results or more can be distinguished from less than the value. In addition, when the test results of both of the limit of detection and the limit of quantification should be obtained, it is desirable that with respect to the ranges serving as the basis, it is possible to distinguish among less than the limit of detection, from the limit of detection or more to less than the limit of quantification, and more than the limit of quantification.

Figure 8:
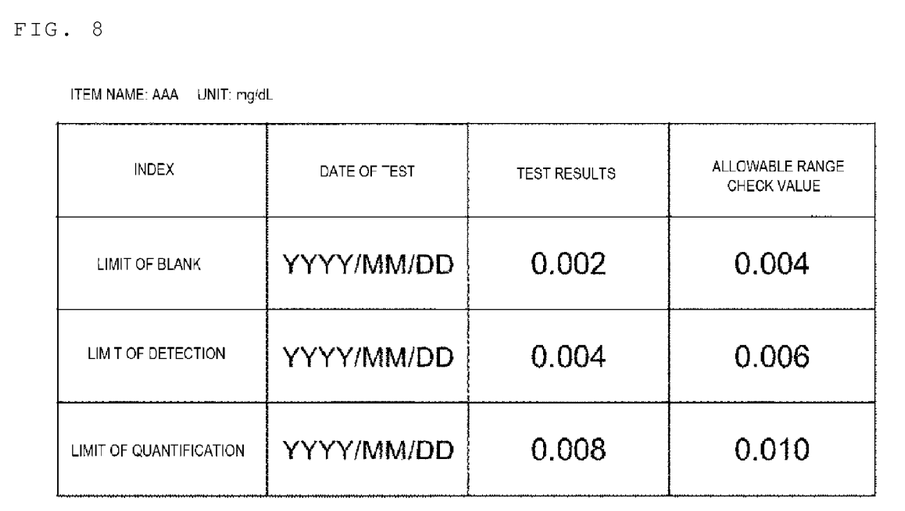
FIG. 8 A diagram showing an example of a screen for setting a check value of an allowable range of the limit of detection/limit of quantification, in an automatic analyzer to which the invention is applied.

FIG. 8 is a diagram showing an example of a screen for setting a check value of an allowable range of the limit of detection/limit of quantification, in an automatic analyzer to which the invention is applied. In FIG. 8, in addition to categories of indexes for the limit of detection/limit of quantification and the dates of test, actual test results and an example of a check value of an allowable range for each index (the rightest column) are shown.

There is a function to output an alarm, when the test results of the limit of detection/limit of quantification exceed the check value of the allowable range. As the check value of the allowable range of the limit of detection/limit of quantification, for example, a standard value for clinical determination, a property value of the lower limit of the measurement range described in the attachment of a reagent, and the like may be input.

A possible constitution is that, by setting check values of allowable ranges of the limit of detection/limit of quantification for more than one item, it is recommended to check whether there is no problem with the reagent when the value of one item exceeds the check value, and it is recommended to check the status of the apparatus and repair the apparatus when the values of more than one item exceed the check values.

The invention has been explained above. In the description, the invention has been explained with examples in which the evaluation test is conducted for both of the limit of detection and the limit of quantification. However, it is not assumed that the evaluation test is always conducted for the both, but the invention can be applied to a case in which the evaluation test is conducted for one of them. In this case, the information regarding one of them should be displayed in FIG. 2 and FIGS. 4 to 8. In addition, although the screen for setting the operation condition of the detection/quantification limit test in FIG. 2, the screen for setting the determination condition of the detection/quantification limit test in FIG. 5, and the screen for setting the provided information of the measurement results/reexamination in FIG. 7 have been explained in separate diagrams, the information in these screens may be displayed in a single screen at the output unit 37 or displayed separately. Any embodiment is acceptable as long as each of the operation condition, determination condition and the like can be set. In addition, although the provided information and the reexamination condition are explained in a single diagram in FIG. 7, they may be set separately.

REFERENCE SIGNS LIST

1 Step for selecting item
2 Step for setting whether test should be conducted or not
3 Step for setting operation interval of test
4 Step for inputting predicted value
5 Step for selecting method for preparing dilution series
6 Step for setting kind of dilution series 7 Step for inputting number of dilution series of dilution series
8 Step for inputting concentration of original sample before dilution
9 Step for setting solvent
10 Step for inputting theoretical concentrations
11 Step for inputting number of repetitive measurements
12 Step for inputting method for determining limit of detection/limit of quantification
13 Box for selecting item name
14 Box for setting whether limit of detection/limit of quantification test should be conducted or not
15 Box for setting operation interval of limit of detection/limit of quantification test
16 Box for setting method for preparing dilution series/number of measurements
17 Sample disk
18 Sample
19 Sample container
20 Reaction disk
21 Reaction container
22 Sample-dispensing mechanism
23 Reagent disk
24 Reagent
25 Reagent container
26 Reagent-dispensing mechanism
27 Stirring mechanism
28 Thermostat bath-circulating liquid
29 Transmitted light measurement unit
30 Scattered light measurement unit
31 Reaction container-washing mechanism
32 Control circuit
33 Transmitted light measurement circuit
34 Scattered light measurement circuit
35 PC
36 Input unit
37 Output unit

The invention claimed is:

1. An automatic analyzer comprising:
a first dispenser to dispense a sample into a plurality of reaction containers;
a second dispenser to dispense a reagent into the reaction containers;
a photometer to measure a mixture of the sample and the reagent in the reaction containers;
a display; and
a processor connected to a memory which stores instructions that, when executed by the processor, cause the processor to:
provide a screen on the display to set operation conditions including a measurement item for analyzing the sample and at least one of an evaluation test for a limit of detection and an evaluation test for a limit of quantification to be conducted for the measurement item and further including a time interval for performing the at least one of the evaluation test for a limit of detection and the evaluation test for a limit of quantification in accordance with user input,
set determination conditions including a determination method, using the screen, from among a plurality of determination methods for each of the at least one of the evaluation test for the limit of detection and the evaluation test for the limit of quantification in accordance with user input,
prepare a first dilution series containing different dilution concentrations of the sample and the reagent in the reaction containers that is prepared for the at least one of the evaluation test for the limit of detection and the evaluation test for the limit of quantification by controlling the first dispenser and the second dispenser based on the set operation conditions,
obtain measurement results of the first dilution series according to the at least one of the evaluation test for the limit of detection and the evaluation test for the limit of quantification by controlling the photometer based on the set operation conditions, and calculating a test result for each of the at least one of the evaluation test for the limit of detection and the evaluation test for the limit of quantification from the measurement results of the first dilution series based on the set determination conditions,
set allowable ranges of the test result for each of the at least one of the evaluation test for the limit of detection and the evaluation test for the limit of quantification, and
output an alarm when the calculated test result for either of the at least one of the evaluation test for the limit of detection and the evaluation test for the limit of quantification exceed the set allowable ranges.

2. The automatic analyzer of claim 1, wherein the memory further stores instructions that, when executed by the processor, cause the processor to:
set reexamination conditions for each of a plurality of ranges for the measurement results for each of the at least one of the evaluation test for the limit of detection and the evaluation test for the limit of quantification in accordance with user input,
prepare a second dilution series containing dilution concentrations of the sample and the reagent in the reaction containers that are higher than the first dilution series by controlling the first dispenser and the second dispenser based on the set operation conditions and the set reexamination conditions,
obtain additional measurement results of the second dilution series for the at least one of the evaluation test for the limit of detection and the evaluation test for the limit of quantification by controlling the photometer based on the calculated test result, the set operation conditions and the set reexamination conditions, and
calculating an additional test result for each of the at least one of the evaluation test for the limit of detection and the evaluation test for the limit of quantification from the additional measurement results of the second dilution series based on the set determination conditions.

3. The automatic analyzer of claim 2, wherein the ranges are set for each of less than a limit of blank, more than the limit of blank and less than the limit of detection, more than the limit of detection and less than the limit of quantification, and more than the limit of quantification.

4. The automatic analyzer of claim 2, wherein the operation conditions are set for both of the evaluation tests, the determination conditions are set for both of the evaluation tests, the measurement results are obtained for both of the evaluation tests, and the test result is calculated for both of the evaluation tests.

5. The automatic analyzer of claim 3, wherein the memory further stores instructions that, when executed by the processor, cause the processor to:
obtain the additional measurement results of the second dilution series when the measurement results are more than the limit of blank and less than the limit of detection, or more than the limit of detection and less than the limit of quantification.

6. The automatic analyzer of claim 2, wherein the memory further stores instructions that, when executed by the processor, cause the processor to:
  automatically prepare the second dilution series of the sample and the reagent in the reaction containers by controlling the first dispenser and the second dispenser based on the set operation conditions and the set reexamination conditions.

7. The automatic analyzer of claim 1, wherein the memory further stores instructions that, when executed by the processor, cause the processor to:
  automatically prepare the first dilution series containing different dilution concentrations of the sample and the reagent in the reaction containers by controlling the first dispenser and the second dispenser based on the interval of the set operation conditions.

* * * * *